(12) United States Patent
Dohrmann et al.

(10) Patent No.: US 11,488,724 B2
(45) Date of Patent: Nov. 1, 2022

(54) SYSTEMS AND METHODS FOR A VIRTUAL, INTELLIGENT AND CUSTOMIZABLE PERSONAL MEDICAL ASSISTANT

(71) Applicant: Electronic Caregiver, Inc., Las Cruces, NM (US)

(72) Inventors: Anthony Dohrmann, Las Cruces, NM (US); Bryan John Chasko, Las Cruces, NM (US); Judah Tveito, Las Cruces, NM (US); David W. Keeley, Frisco, TX (US)

(73) Assignee: Electronic Caregiver, Inc., Las Cruces, NM (US)

( * ) Notice: Subject to any disclaimer, the term of this patent is extended or adjusted under 35 U.S.C. 154(b) by 643 days.

(21) Appl. No.: 16/416,062

(22) Filed: May 17, 2019

(65) Prior Publication Data

US 2019/0385749 A1    Dec. 19, 2019

Related U.S. Application Data

(60) Provisional application No. 62/686,325, filed on Jun. 18, 2018.

(51) Int. Cl.
| | |
|---|---|
| *G16H 70/00* | (2018.01) |
| *G06F 9/54* | (2006.01) |
| *G06F 9/451* | (2018.01) |
| *G16H 20/60* | (2018.01) |

(52) U.S. Cl.
CPC ............. *G16H 70/00* (2018.01); *G06F 9/453* (2018.02); *G06F 9/542* (2013.01); *G16H 20/60* (2018.01)

(58) Field of Classification Search
CPC ........ G16H 70/00; G16H 20/60; G06F 9/453; G06F 9/542
USPC ........................................................ 705/2–3
See application file for complete search history.

(56) References Cited

U.S. PATENT DOCUMENTS

| | | | |
|---|---|---|---|
| 5,211,642 A | 5/1993 | Clendenning | |
| 5,475,953 A | 12/1995 | Greenfield | |
| 6,665,647 B1 | 12/2003 | Haudenschild | |
| 7,233,872 B2 | 6/2007 | Shibasaki et al. | |
| 7,445,086 B1 | 11/2008 | Sizemore | |
| 7,612,681 B2 | 11/2009 | Azzaro et al. | |
| 7,971,141 B1 | 6/2011 | Quinn et al. | |
| 8,206,325 B1 | 6/2012 | Najafi et al. | |
| 8,771,206 B2 | 7/2014 | Gettelman et al. | |
| 9,317,916 B1 | 4/2016 | Hanina et al. | |

(Continued)

FOREIGN PATENT DOCUMENTS

| | | |
|---|---|---|
| AU | 2019240484 B2 | 11/2021 |
| CA | 2949449 A1 | 11/2015 |

(Continued)

OTHER PUBLICATIONS

Wang et al. "Augmented Reality as a Telemedicine Platform for Remote Procedural Training." Sensors (Basel, Switzerland) vol. 17,10 2294. Oct. 10, 2017, doi:10.3390/s17102294 (Year: 2017).*

(Continued)

*Primary Examiner* — Joy Chng
(74) *Attorney, Agent, or Firm* — Carr & Ferrell LLP

(57) ABSTRACT

Embodiments of the present technology pertain to methods and systems for a voice based, intelligent, augmented reality (AR) based on-demand medical assistant receiving health data of a user using medical testing equipment.

19 Claims, 11 Drawing Sheets

(56) References Cited

U.S. PATENT DOCUMENTS

| | | |
|---|---|---|
| 9,591,996 B2 | 3/2017 | Chang et al. |
| 9,972,187 B1 | 5/2018 | Srinivasan et al. |
| 10,387,963 B1 | 8/2019 | Leise et al. |
| 10,628,635 B1 | 4/2020 | Carpenter, II et al. |
| 10,761,691 B2 | 9/2020 | Anzures et al. |
| 10,813,572 B2 | 10/2020 | Dohrmann et al. |
| 11,113,943 B2 | 9/2021 | Wright et al. |
| 11,213,224 B2 | 1/2022 | Dohrmann et al. |
| 2002/0062342 A1 | 5/2002 | Sidles |
| 2002/0196944 A1 | 12/2002 | Davis et al. |
| 2004/0109470 A1 | 6/2004 | Derechin et al. |
| 2005/0035862 A1 | 2/2005 | Wildman et al. |
| 2005/0055942 A1 | 3/2005 | Maelzer et al. |
| 2007/0032929 A1 | 2/2007 | Yoshioka |
| 2007/0238936 A1 | 10/2007 | Becker |
| 2008/0010293 A1 | 1/2008 | Zpevak et al. |
| 2008/0186189 A1 | 8/2008 | Azzaro et al. |
| 2009/0094285 A1 | 4/2009 | Mackie et al. |
| 2010/0124737 A1 | 5/2010 | Panzer |
| 2011/0126207 A1 | 5/2011 | Wipfel et al. |
| 2011/0145018 A1 | 6/2011 | Fotsch et al. |
| 2011/0232708 A1 | 9/2011 | Kemp |
| 2012/0025989 A1 | 2/2012 | Cuddihy et al. |
| 2012/0075464 A1 | 3/2012 | Derenne et al. |
| 2012/0120184 A1 | 5/2012 | Fornell et al. |
| 2012/0121849 A1 | 5/2012 | Nojima |
| 2012/0154582 A1 | 6/2012 | Johnson et al. |
| 2012/0165618 A1 | 6/2012 | Algoo et al. |
| 2012/0179067 A1 | 7/2012 | Wekell |
| 2012/0179916 A1 | 7/2012 | Staker et al. |
| 2012/0229634 A1 | 9/2012 | Laett et al. |
| 2012/0253233 A1 | 10/2012 | Greene et al. |
| 2013/0000228 A1 | 1/2013 | Ovaert |
| 2013/0060167 A1 | 2/2013 | Dracup |
| 2013/0127620 A1 | 5/2013 | Siebers et al. |
| 2013/0145449 A1 | 6/2013 | Busser et al. |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0128691 A1 | 5/2014 | Olivier |
| 2014/0148733 A1 | 5/2014 | Stone et al. |
| 2014/0171039 A1 | 6/2014 | Bjontegard |
| 2014/0171834 A1 | 6/2014 | DeGoede et al. |
| 2014/0232600 A1 | 8/2014 | Larose et al. |
| 2014/0243686 A1 | 8/2014 | Kimmel |
| 2014/0257852 A1 | 9/2014 | Walker et al. |
| 2014/0267582 A1 | 9/2014 | Beutter et al. |
| 2014/0278605 A1 | 9/2014 | Borucki et al. |
| 2014/0330172 A1 | 11/2014 | Jovanov et al. |
| 2014/0337048 A1* | 11/2014 | Brown .................. G16H 50/20 705/2 |
| 2014/0358828 A1 | 12/2014 | Phillipps et al. |
| 2014/0368601 A1 | 12/2014 | deCharms |
| 2015/0019250 A1 | 1/2015 | Goodman et al. |
| 2015/0109442 A1 | 4/2015 | Derenne et al. |
| 2015/0169835 A1 | 6/2015 | Hamdan et al. |
| 2015/0359467 A1 | 12/2015 | Tran |
| 2016/0026354 A1 | 1/2016 | McIntosh et al. |
| 2016/0117470 A1 | 4/2016 | Welsh et al. |
| 2016/0117484 A1 | 4/2016 | Hanina et al. |
| 2016/0154977 A1 | 6/2016 | Jagadish et al. |
| 2016/0217264 A1 | 7/2016 | Sanford |
| 2016/0253890 A1 | 9/2016 | Rabinowitz et al. |
| 2016/0267327 A1 | 9/2016 | Franz et al. |
| 2016/0314255 A1 | 10/2016 | Cook et al. |
| 2017/0000387 A1 | 1/2017 | Forth et al. |
| 2017/0000422 A1* | 1/2017 | Moturu ................ A61B 5/0022 |
| 2017/0024531 A1 | 1/2017 | Malaviya |
| 2017/0055917 A1 | 3/2017 | Stone et al. |
| 2017/0140631 A1 | 5/2017 | Pietrocola et al. |
| 2017/0147154 A1 | 5/2017 | Steiner et al. |
| 2017/0192950 A1 | 7/2017 | Gaither et al. |
| 2017/0193163 A1 | 7/2017 | Melle et al. |
| 2017/0197115 A1 | 7/2017 | Cook et al. |
| 2017/0213145 A1 | 7/2017 | Pathak et al. |
| 2017/0273601 A1 | 9/2017 | Wang et al. |
| 2017/0337274 A1 | 11/2017 | Ly et al. |
| 2017/0344706 A1 | 11/2017 | Torres et al. |
| 2017/0344832 A1 | 11/2017 | Leung et al. |
| 2018/0005448 A1 | 1/2018 | Choukroun et al. |
| 2018/0075558 A1 | 3/2018 | Hill, Sr. et al. |
| 2018/0154514 A1* | 6/2018 | Angle .................... G05D 1/021 |
| 2018/0165938 A1 | 6/2018 | Honda et al. |
| 2018/0182472 A1 | 6/2018 | Preston et al. |
| 2018/0189756 A1 | 7/2018 | Purves et al. |
| 2018/0322405 A1 | 11/2018 | Fadell et al. |
| 2018/0360349 A9 | 12/2018 | Dohrmann et al. |
| 2018/0368780 A1 | 12/2018 | Bruno et al. |
| 2019/0029900 A1 | 1/2019 | Walton et al. |
| 2019/0042700 A1 | 2/2019 | Alotaibi |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0282130 A1 | 9/2019 | Dohrmann et al. |
| 2019/0286942 A1 | 9/2019 | Abhiram et al. |
| 2019/0311792 A1 | 10/2019 | Dohrmann et al. |
| 2019/0318165 A1 | 10/2019 | Shah et al. |
| 2020/0101969 A1 | 4/2020 | Natroshvili et al. |
| 2020/0251220 A1 | 8/2020 | Chasko |
| 2020/0357256 A1 | 11/2020 | Wright et al. |
| 2020/0357511 A1 | 11/2020 | Sanford |
| 2021/0007631 A1 | 1/2021 | Dohrmann et al. |
| 2021/0273962 A1 | 9/2021 | Dohrmann et al. |
| 2021/0358202 A1 | 11/2021 | Tveito et al. |
| 2021/0398410 A1 | 12/2021 | Wright et al. |
| 2022/0022760 A1 | 1/2022 | Salcido et al. |
| 2022/0117515 A1 | 4/2022 | Dohrmann et al. |

FOREIGN PATENT DOCUMENTS

| | | |
|---|---|---|
| CN | 104361321 A | 2/2015 |
| CN | 106056035 A | 10/2016 |
| CN | 107411515 A | 12/2017 |
| CN | 111801645 A | 10/2020 |
| CN | 111801939 A | 10/2020 |
| CN | 111867467 A | 10/2020 |
| CN | 113795808 | 12/2021 |
| EP | 3740856 A1 | 11/2020 |
| EP | 3756344 A1 | 12/2020 |
| EP | 3768164 A1 | 1/2021 |
| EP | 3773174 A1 | 2/2021 |
| EP | 3815108 A1 | 5/2021 |
| EP | 3920797 A1 | 12/2021 |
| EP | 3944258 | 1/2022 |
| EP | 3966657 A | 3/2022 |
| IN | 202027033318 A | 10/2020 |
| IN | 202027035634 A | 10/2020 |
| IN | 202127033278 A | 8/2021 |
| JP | 2002304362 A | 10/2002 |
| JP | 2005228305 A | 8/2005 |
| JP | 2010172481 A | 8/2010 |
| JP | 2012232652 A | 11/2012 |
| JP | 2016137226 A | 8/2016 |
| JP | 2016525383 A | 8/2016 |
| JP | 2021510881 A | 4/2021 |
| JP | 2021524075 A | 9/2021 |
| JP | 2022519283 A | 3/2022 |
| KR | 1020160040078 A | 4/2016 |
| KR | 1020200105519 A | 9/2020 |
| KR | 1020200121832 A | 10/2020 |
| KR | 1020200130713 A | 11/2020 |
| WO | WO2000005639 A2 | 2/2000 |
| WO | WO2014043757 A1 | 3/2014 |
| WO | WO2017118908 A1 | 7/2017 |
| WO | WO2018032089 A1 | 2/2018 |
| WO | WO2019143397 A1 | 7/2019 |

(56) References Cited

FOREIGN PATENT DOCUMENTS

| WO | WO2019164585 A1 | 8/2019 |
|---|---|---|
| WO | WO2019182792 A1 | 9/2019 |
| WO | WO2019199549 A1 | 10/2019 |
| WO | WO2019245713 A1 | 12/2019 |
| WO | WO2020163180 A1 | 8/2020 |
| WO | WO2020227303 A1 | 11/2020 |

OTHER PUBLICATIONS

Gutierrez et al., "PHARA: A Personal Health Augmented Reality Assistant To Support Decision-Making At Grocery Stores," International Workshop On Health Recommender Systems, Aug. 2017, pp. 1-4, http://ceur-ws.org/Vol-1953/healthRecSys17_paper_7.pdf (Year: 2017).*
"International Search Report" and "Written Opinion of the International Searching Authority," Patent Cooperation Treaty Application No. PCT/US2020/031486, dated Aug. 3, 2020, 7 pages.
"International Search Report" and "Written Opinion of the International Searching Authority," Patent Cooperation Treaty Application No. PCT/US2020/016248, dated May 11, 2020, 7 pages.
"Office Action", Australia Patent Application No. 2019240484, dated Nov. 13, 2020, 4 pages.
Rosen et al., "Slipping and Tripping: Fall Injuries in Adults Associated with Rugs and Carpets," Journal of Injury & Violence Research, 5(1), (2013), pp. 61-69.
Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.
Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.
Bellemare et al., A Distributional Perspective on Reinforcement Learning:, Proceedings of the 34th International Conference on Machine Learning, Sydney, Australia, Jul. 21, 2017, 19 pages.
Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS One 4(7): e6421>, 13 pages.
Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2018/057814, dated Jan. 11, 2019, 9 pages.
"International Search Report" and "Written Opinion of the International Searching Authority," Patent Cooperation Treaty Application No. PCT/US2018/068210, dated Apr. 12, 2019, 9 pages.
"International Search Report" and "Written Opinion of the International Searching Authority," Patent Cooperation Treaty Application No. PCT/US2019/021678, dated May 24, 2019, 12 pages.
"International Search Report" and "Written Opinion of the International Searching Authority," Patent Cooperation Treaty Application No. PCT/US2019/025652, dated Jul. 18, 2019, 11 pages.
"International Search Report" and "Written Opinion of the International Searching Authority," Patent Cooperation Treaty Application No. PCT/US2019/034206, dated Aug. 1, 2019, 11 pages.
"Office Action", Australia Patent Application No. 2018403182, dated Feb. 5, 2021, 5 pages.
"Office Action", Australia Patent Application No. 2018409860, dated Feb. 10, 2021, 4 pages.
Leber, Jessica, "The Avatar Will See You Now", MIT Technology Review, Sep. 17, 2013, 4 pages.
"Office Action", India Patent Application No. 202027035634, dated Jun. 30, 2021, 10 pages.
"Office Action", India Patent Application No. 202027033121, dated Jul. 29, 2021, 7 pages.
"Office Action", Canada Patent Application No. 3088396, dated Aug. 6, 2021, 7 pages.
"Office Action", China Patent Application No. 201880089608.2, dated Aug. 3, 2021, 8 pages.
"Office Action", Japan Patent Application No. 2020-543924, dated Jul. 27, 2021, 3 pages [6 pages with translation].
"Office Action", Australia Patent Application No. 2019240484, dated Aug. 2, 2021, 3 pages.
"Office Action", Canada Patent Application No. 3089312, dated Aug. 19, 2021, 3 pages.
"Office Action", Singapore Patent Application No. 11202008201P, dated Apr. 4, 2022, 200 pages.
"Office Action", India Patent Application No. 202127033278, dated Apr. 20, 2022, 7 pages.
"Office Action", Canada Patent Application No. 3088396, dated May 6, 2022, 4 pages.
"Extended European Search Report", European Patent Application No. 18901139.8, dated Sep. 9, 2021, 6 pages.
"Office Action", Canada Patent Application No. 3091957, dated Sep. 14, 2021, 4 pages.
"Office Action", Japan Patent Application No. 2020-540382, dated Aug. 24, 2021, 7 pages [13 pages with translation].
"Extended European Search Report", European Patent Application No. 18907032.9, dated Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcisiegen.de/wp-uploads/2014/05/isCtutorial.doku.pdf>, Mar. 30, 2013, 36 pages.
"Notice of Allowance", Australia Patent Application No. 2019240484, dated Oct. 27, 2021, 4 pages.
"Extended European Search Report", European Patent Application No. 19772545.0, dated Nov. 16, 2021, 8 pages.
"Office Action", India Patent Application No. 202027033318, dated Nov. 18, 2021, 6 pages.
"Office Action", Australia Patent Application No. 2018409860, dated Nov. 30, 2021, 4 pages.
"Office Action", Australia Patent Application No. 2018403182, dated Dec. 1, 2021, 3 pages.
"Office Action", Korea Patent Application No. 10-2020-7028606, dated Oct. 29, 2021, 7 pages [14 pages with translation].
"Office Action", Japan Patent Application No. 2020-543924, dated Nov. 24, 2021, 3 pages [6 pages with translation].
"Extended European Search Report", European Patent Application No. EP19785057, dated Dec. 6, 2021, 8 pages.
"Office Action", Australia Patent Application No. 2020218172, dated Dec. 21, 2021, 4 pages.
"Extended European Search Report", European Patent Application No. 21187314.6, dated Dec. 10, 2021, 10 pages,.
"Notice of Allowance", Australia Patent Application No. 2018403182, dated Jan. 20, 2022, 4 pages.
"Office Action", Australia Patent Application No. 2018409860, dated Jan. 24, 2022, 5 pages.
"Office Action", China Patent Application No. 201880089608.2, dated Feb. 8, 2022, 6 pages (15 pages with translation).
"International Search Report" and "Written Opinion of the International Searching Authority," Patent Cooperation Treaty Application No. PCT/US2021/056060, dated Jan. 28, 2022, 8 pages.
"Extended European Search Report", European Patent Application No. 19822930.4, dated Feb. 15, 2022, 9 pages.
"Office Action", Japan Patent Application No. 2020-550657, dated Feb. 8, 2022, 8 pages.

* cited by examiner

SYSTEMS AND METHODS FOR A VIRTUAL, INTELLIGENT AND CUSTOMIZABLE PERSONAL MEDICAL ASSISTANT

CROSS REFERENCE TO RELATED APPLICATIONS

This application claims the priority benefit of U.S. Provisional Patent Application Ser. No. 62/686,325 filed on Jun. 18, 2018 and titled "Virtual, Intelligent and Customizable Personal Medical Assistant," which is hereby incorporated by reference in its entirety.

FIELD OF THE TECHNOLOGY

Embodiments of the present technology relate to systems and methods for a voice based, intelligent, augmented reality (AR) based on-demand medical assistant.

SUMMARY

According to some embodiments, the present technology is directed to methods for a voice based, intelligent, augmented reality (AR) based on-demand medical assistant. In some embodiments the method comprises: (a) receiving health data of a user using medical testing equipment; (b) storing the health data of the user in a retrieval database; (c) receiving an audio input using a web-browser based AR, animated, conversational graphical user interface, the audio input comprising keywords; (d) determining a domain of use based on processing the keywords of the audio input; (e) processing the health data of the user, the keywords, and the domain of use to determine a medical assessment for the user; (f) determining personalized medical services for the user based on the medical assessment; (g) providing the user with access to the personalized medical services using the web-browser based AR, animated, conversational graphical user interface; and (h) displaying a status of the personalized medical services to the user using the web-browser based AR, animated, conversational graphical user interface.

In some embodiments of the present technology, the methods further comprise actively prompting the user for health data using the web-browser based AR, animated, conversational graphical user interface.

In some embodiments the processing the health data of the user, the keywords, and the domain of use utilizes a medical and health vocabulary database.

In various embodiments the processing the health data of the user, the keywords, and the domain of use utilizes a secure cloud-based repository of user provided data, a public domain medical and health database, and a public domain informational repository.

In some embodiments the health data of a user comprises a baseline health level of the user.

In some embodiments of the present technology, the methods further comprise determining when the baseline health level of the user deviates from a predetermined threshold.

In some embodiments of the present technology, the methods further comprise displaying an alert to the user when the baseline health level of the user changes past a threshold via the web-browser based AR, animated, conversational graphical user interface.

In various embodiments of the present technology, the methods further comprise sending an alert to a third-party medical service provider when the baseline health level of the user deviates from the predetermined threshold.

In some embodiments the health data of the user comprises a disease profile of the user.

In various embodiments of the present technology, the methods further comprise providing the user with a treatment plan specific the disease profile of the user using the web-browser based AR, animated, conversational graphical user interface.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

DETAILED DESCRIPTION

In the following description, for purposes of explanation, numerous specific details are set forth in order to provide a thorough understanding of the disclosure. It will be apparent, however, to one skilled in the art, that the disclosure may be practiced without these specific details. In other instances, structures and devices may be shown in block diagram form only in order to avoid obscuring the disclosure. It should be understood that the disclosed embodiments are merely exemplary of the invention, which may be embodied in multiple forms. Those details disclosed herein are not to be interpreted in any form as limiting, but as the basis for the claims.

According to the embodiments of the present technology, an automated, voice based and intelligent AR virtual medical assistant is by way of an electronic device. This medical assistant facilitates user interaction with the device to assist the user with various home healthcare activities. The medical assistant is integrated into the environment of the user and utilizes conversational platforms to achieve the following: access to various external services, providing reminders associated with various user medical needs, obtaining relevant medical information associated with the user, and providing appropriate feedback based on various medical information collected.

In various embodiments the present technology provides a user with continuous access to a virtual care provider via interaction with connected devices of the user. Embodiments of the present technology function to provide quick responses to a variety of health care related inquiries and tasks and relay requested and necessary information/materials to individuals via the display of a user's connected devices. Additionally, the capability of having Internet or cellular network connectivity allows the virtual health assistant to connect users with 24/7 telehealth service, 24/7 emergency monitoring and dispatch capabilities, monitored medication and medical test reminders and provide immediate response to failures associated with user provided medication compliance responses. The addition of ancillary hardware provides the capability for the virtual health assistant to assess and interpret user activity levels, respond to inactivity and falls, deliver questionnaire type health assessments, track symptoms and monitor for potential changes in condition. For example, these capabilities allow the virtual health assistant to effectively provide methods and systems for continued care and monitoring for the user.

Figure 1:
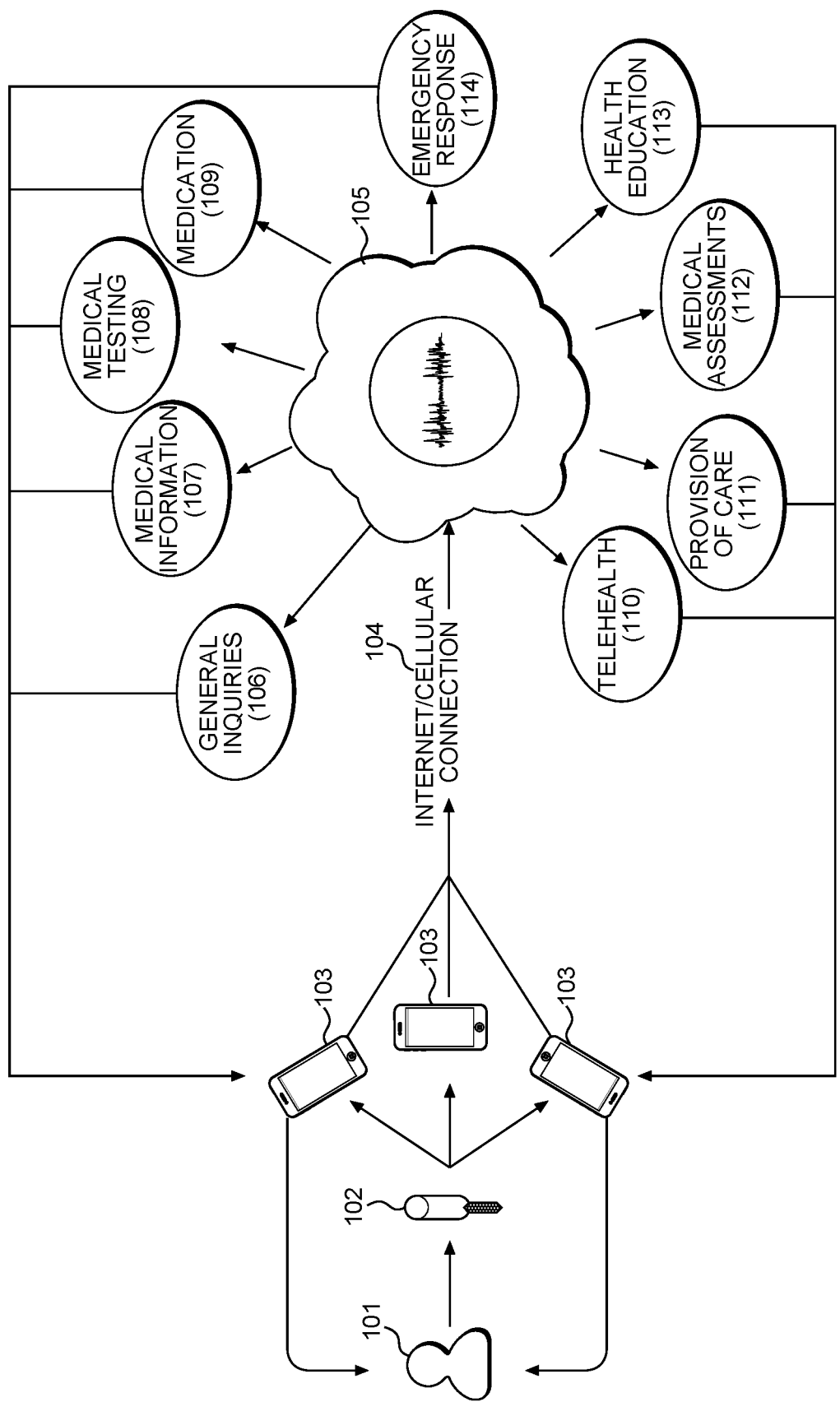
FIG. 1 shows a diagram of system architecture for an exemplary system configured to provide a voice based, intelligent, augmented reality (AR) based on-demand medical assistant according to embodiments of the present technology.

FIG. 1 shows a diagram of system architecture for an exemplary system configured to provide a voice based, intelligent, augmented reality (AR) based on-demand medical assistant according to embodiments of the present technology. FIG. 1 shows an augmented reality based virtual health assistant system. As such, the user 101 utilizes the mechanism for voice input 102 to communicate with a connected device 103 (e.g., mobile device). The connected device 103 is connected to a network. For example, an internet/cellular connection 104. The network (e.g., internet/cellular connection 104) may include a wireless or wire network, or a combination thereof. For example, the network may include one or more of the following: the Internet, local intranet, PAN (Personal Area Network), LAN (Local Area Network), WAN (Wide Area Network), MAN (Metropolitan Area Network), virtual private network (VPN), storage area network (SAN), frame relay connection, Advanced Intelligent Network (AIN) connection, synchronous optical network (SONET) connection, digital T1, T3, E1 or E3 line, Digital Data Service (DDS) connection, DSL (Digital Subscriber Line) connection, Ethernet connection, ISDN (Integrated Services Digital Network) line, dial-up port such as a V.90, V.34 or V.34bis analog modem connection, cable modem, ATM (Asynchronous Transfer Mode) connection, or an FDDI (Fiber Distributed Data Interface) or CDDI (Copper Distributed Data Interface) connection. Furthermore, the communications may also include links to any of a variety of wireless networks including, WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS, CDPD (cellular digital packet data), RIM (Research in Motion, Limited) duplex paging network, Bluetooth radio, or an IEEE 802.11-based radio frequency network. The network can further include or interface with any one or more of the following: RS-232 serial connection, IEEE-1394 (Firewire) connection, Fiber Channel connection, IrDA (infrared) port, SCSI (Small Computer Systems Interface) connection, USB (Universal Serial Bus) connection, or other wired or wireless, digital or analog interface or connection, mesh or Digi® networking.

In various embodiments of the present technology the internet/cellular connection 104 allows voice input from user 101 to be analyzed by a cloud-based keyword processor 105 and directed to an appropriate domain of inquiry. The domains of inquiry associated with the system may include, but are not limited to areas such as general inquiries 106, medical information 107, medical testing 108, medication 109, telehealth 110, provision of care 111, medical assessments 112, health education 113 and emergency response services 114. Following direction to the appropriate domain of inquiry, cloud-based compute power of the present technology executes the query submitted by user 101 and the appropriate service output is provided to user 101 using the connected device 103.

Various embodiments of the present technology are available across a wide variety of devices with voice input technology, internet and/or cellular connectivity, and web-browser capabilities. Systems of the present technology may be implemented with many different types of devices and operational modes. One of ordinary skill in the art associated with the present technology understands that the devices (e.g., connected device 103) and operational modes indicated above are simply examples and are not intended to be exhaustive. As such, it is understood that the present technology may be implemented across additional media meeting the necessary requirements and deployed across a variety of operational modes.

Figure 2:
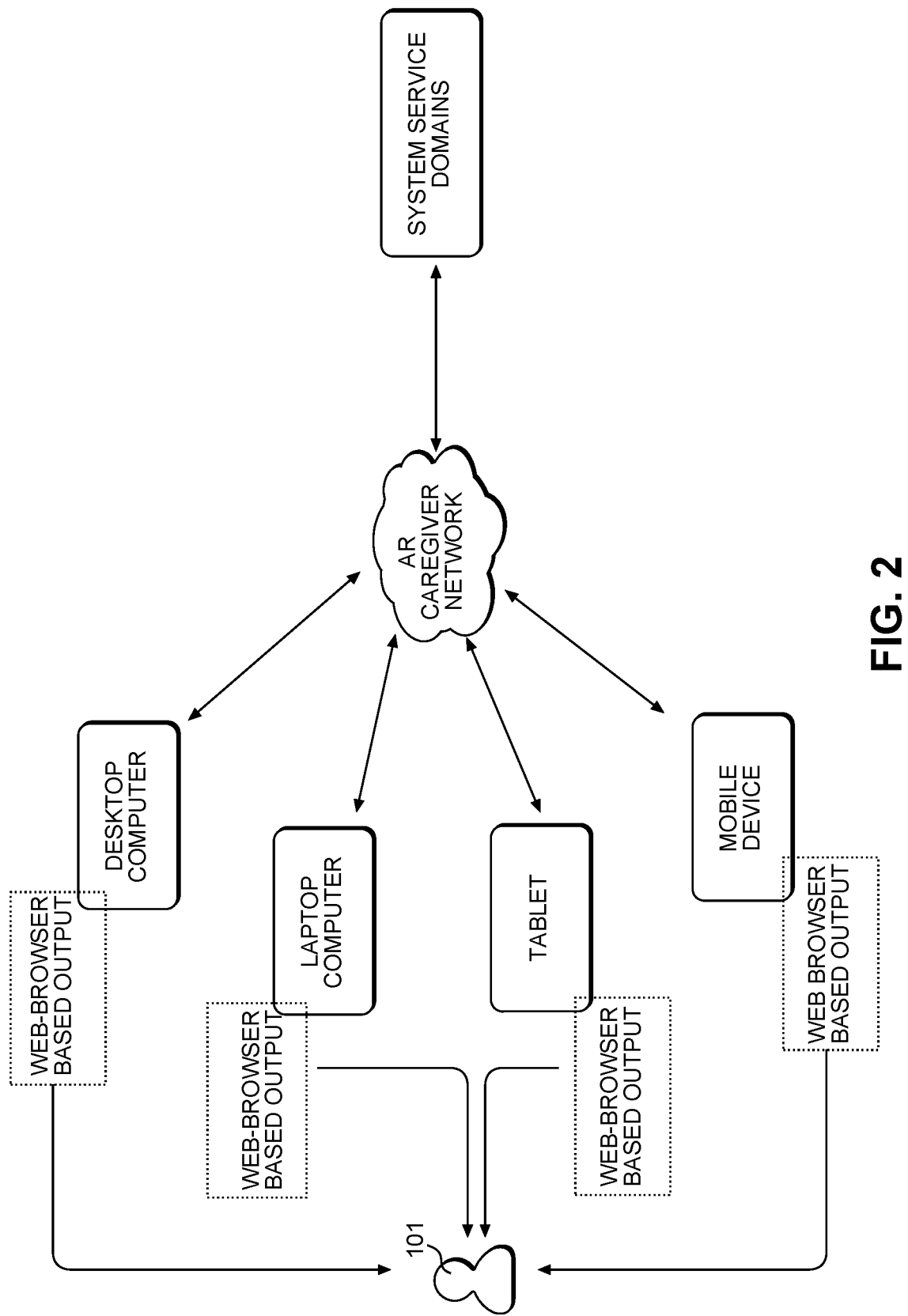
FIG. 2 shows devices for a voice based, intelligent, augmented reality (AR) based on-demand medical assistant according to embodiments of the present technology.

FIG. 2 shows devices for a voice based, intelligent, augmented reality (AR) based on-demand medical assistant according to embodiments of the present technology. FIG. 2 shows a block diagram depicting a system capable of being available on a number of different device types with a web-browser based output. For example, the user 101 may access a desktop computer, a laptop computer, a tablet, and a mobile device that are connected to an AR caregiver network and system service domains.

Figure 3:
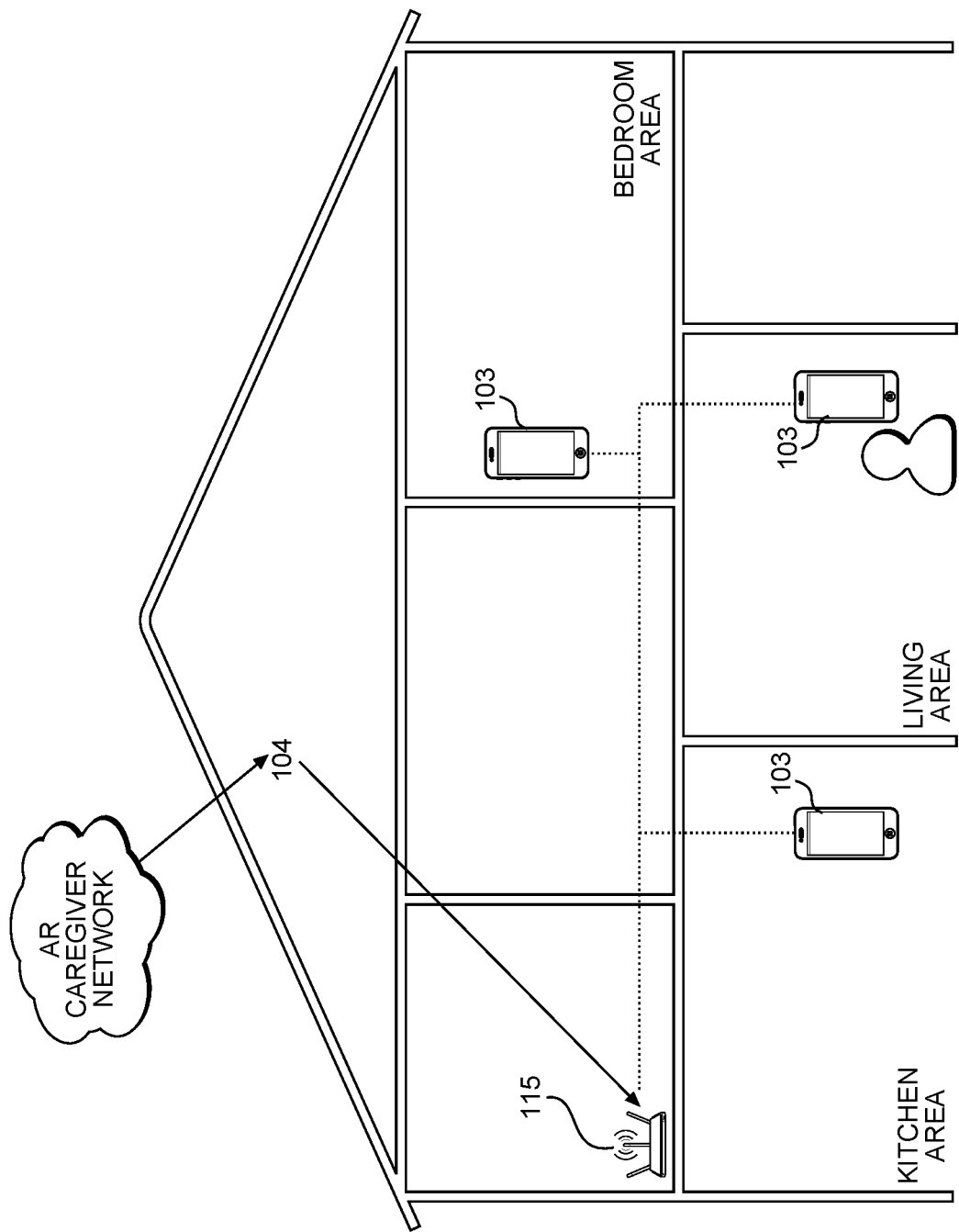
FIG. 3 shows embodiments of a voice based, intelligent, augmented reality (AR) based on-demand medical assistant displayed in a home according to embodiments of the present technology.

FIG. 3 shows embodiments of a voice based, intelligent, augmented reality (AR) based on-demand medical assistant displayed in a home according to embodiments of the present technology. FIG. 3 shows a representation of systems of the present technology functioning across the operational mode utilized in a household setting. In a household setting operational mode, multiple devices can be distributed throughout the house while connected to a router 115 connected to the internet/cellular connection 104 (e.g., a network). In addition, systems of the present technology have capacity to function while user 101 is in transit by way of connection only to a cellular network. Systems of the present technology are capable of providing the user 101 with constant access to the variety of services according to various embodiments.

Figure 4:
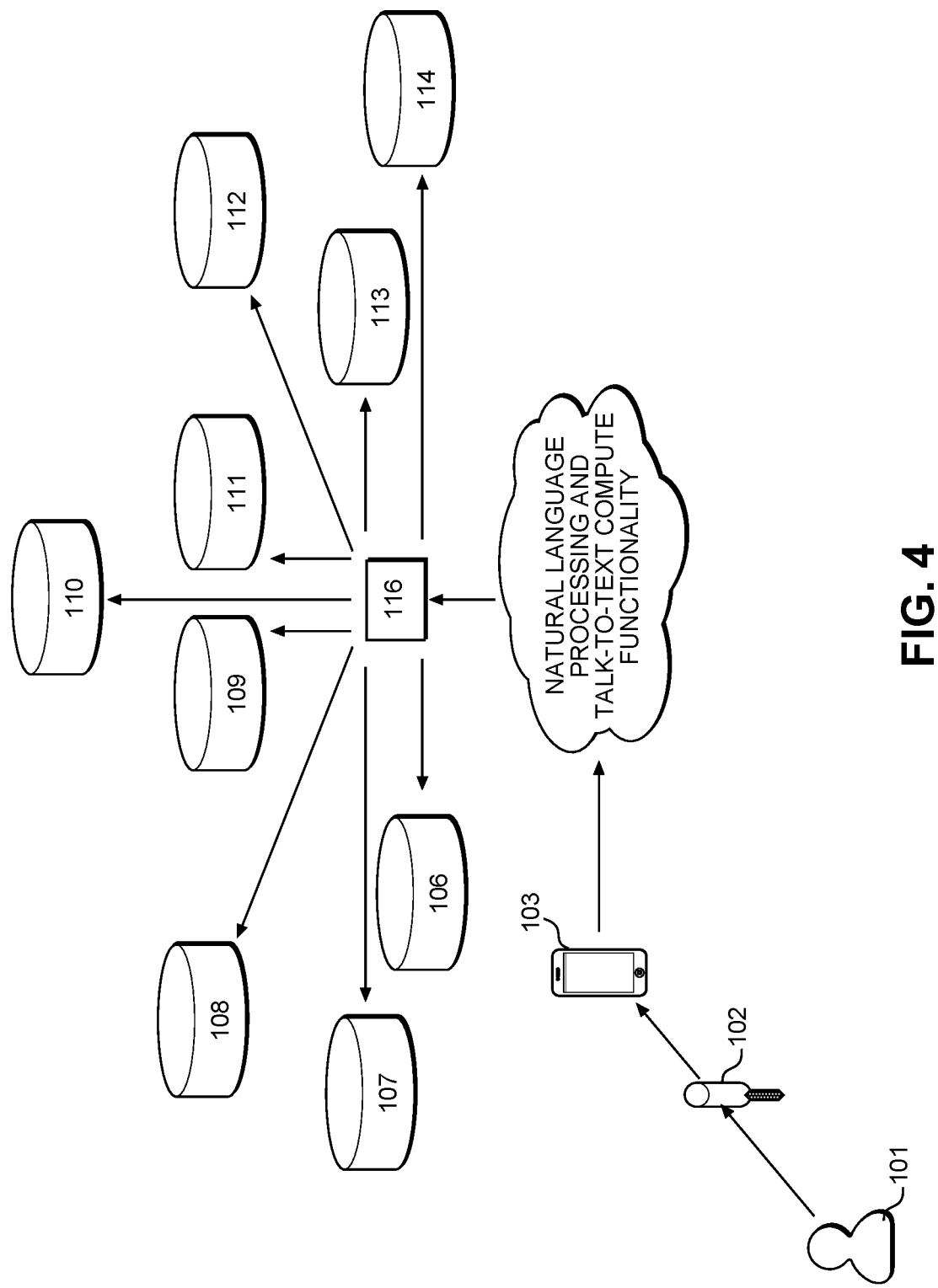
FIG. 4 shows keyword identification functionality according to embodiments of the present technology.

FIG. 4 shows keyword identification functionality according to embodiments of the present technology. FIG. 4 shows embodiments of the present technology are capable of processing voice input data from user 101 such that keywords are identified. Keyword identification from voice input allows the intelligent medical assistant system to quickly access a domain of service desired by user 101 and to carry out a requested function. As such, when the user 101 initiates interactions with systems of the present technology, cloud-based speech-to-text technology converts the user input to text, with the text then being compared to pre-defined keywords stored in a keyword database 116. Upon system recognition of a keyword, the content domain associated with the request of user 101 is accessed. An example is described in FIG. 5. The domains of inquiry associated with the keyword database 116 may include, but are not limited to areas such as general inquiries 106, medical information 107, medical testing 108, medication 109, telehealth 110, provision of care 111, medical assessments 112, health education 113 and emergency response services 114. Following direction to the appropriate domain of inquiry, cloud-based compute power of the present technology executes the query submitted by user 101 and the appropriate service output is provided to user 101 using the connected device 103.

Figure 5:
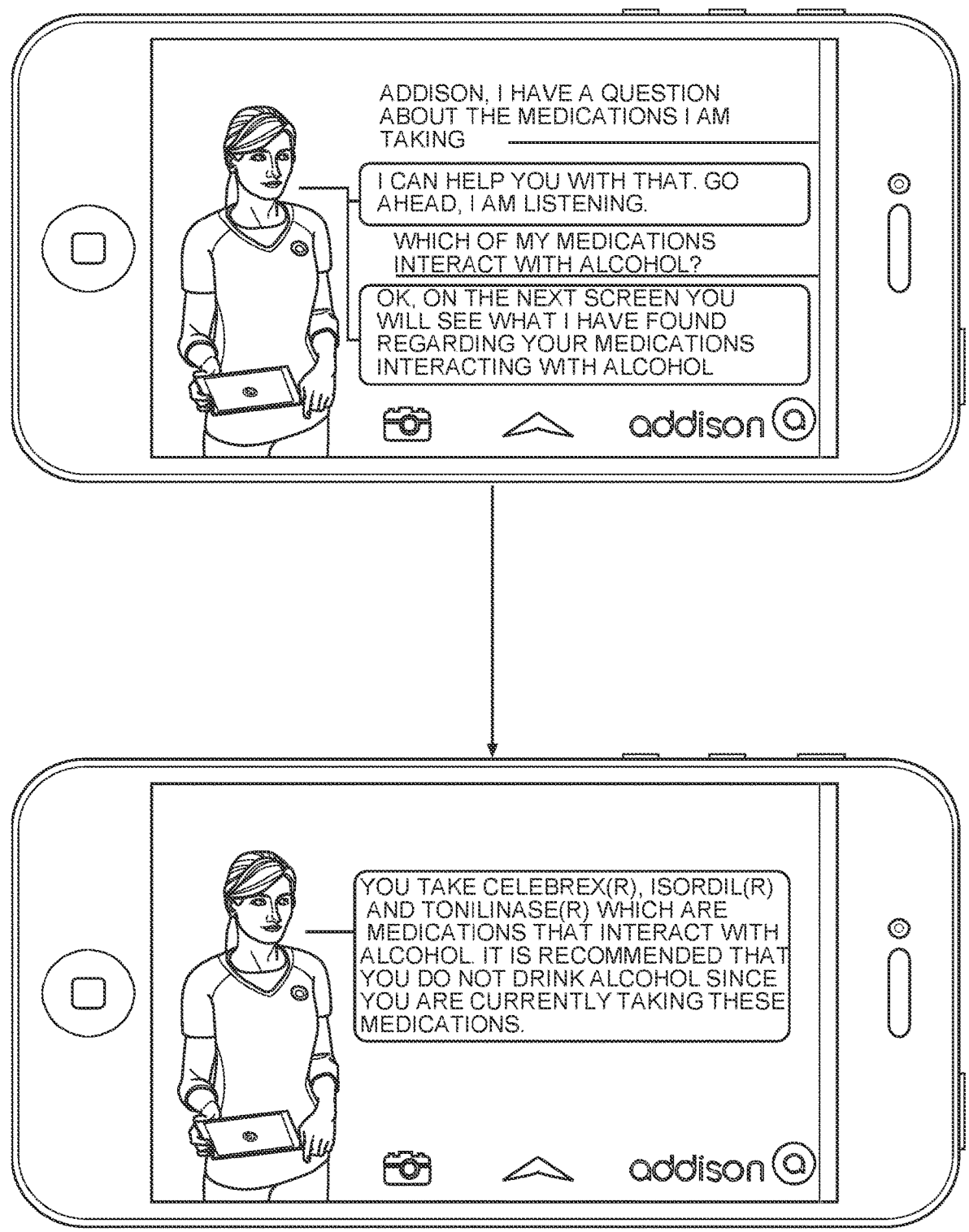
FIG. 5 illustrates exemplary graphical user interfaces for general medication requirements using a voice based, intelligent, augmented reality (AR) based on-demand medical assistant according to embodiments of the present technology.

FIG. 5 illustrates exemplary graphical user interfaces for general medication requirements using a voice based, intelligent, augmented reality (AR) based on-demand medical assistant according to embodiments of the present technology. FIG. 5 shows an example of the user 101 interacting with the system described in FIG. 4. For example, the user 101 initiates interaction with the system by stating the audio input "Addison, I have a question about a medication I am taking." Following this statement by the user 101, the system will process, transmit, and analyze the statement against the various pre-defined keywords stored in the keyword database 116. Upon identifying the pre-defined keyword "medication", the pathway within the system associated with medication data of the user 101 will be activated and the user 101 will be prompted to begin their medication query. The user 101 will then state a query (i.e., audio input) such as "Addison, which of my medications interact with alcohol?". Following this query (i.e., audio input), activation of the medication interaction application programming interface (API) call occurs in a manner resulting in a drug-alcohol interaction search that is specific to those medications consumed by the user 101. Following the drug-alcohol interaction search, the results are provided back to the user in via a web-browser based augmented reality (AR) platform and conversational interface displayed in FIG. 5.

Figure 6A:
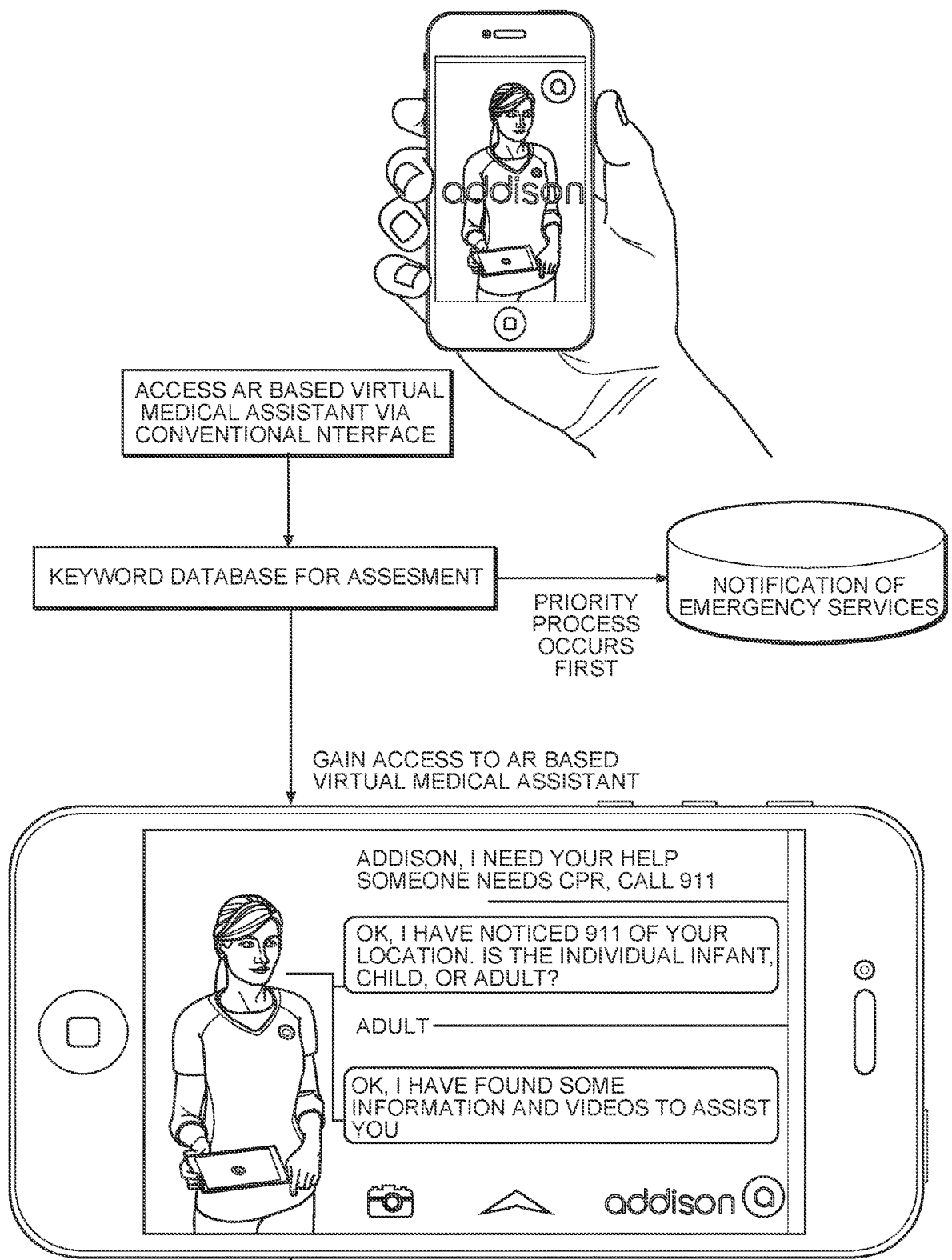
FIG. 6A and FIG. 6B illustrate exemplary graphical user interfaces for provision of emergency medical actions using a voice based, intelligent, augmented reality (AR) based on-demand medical assistant according to embodiments of the present technology.
Figure 6B:
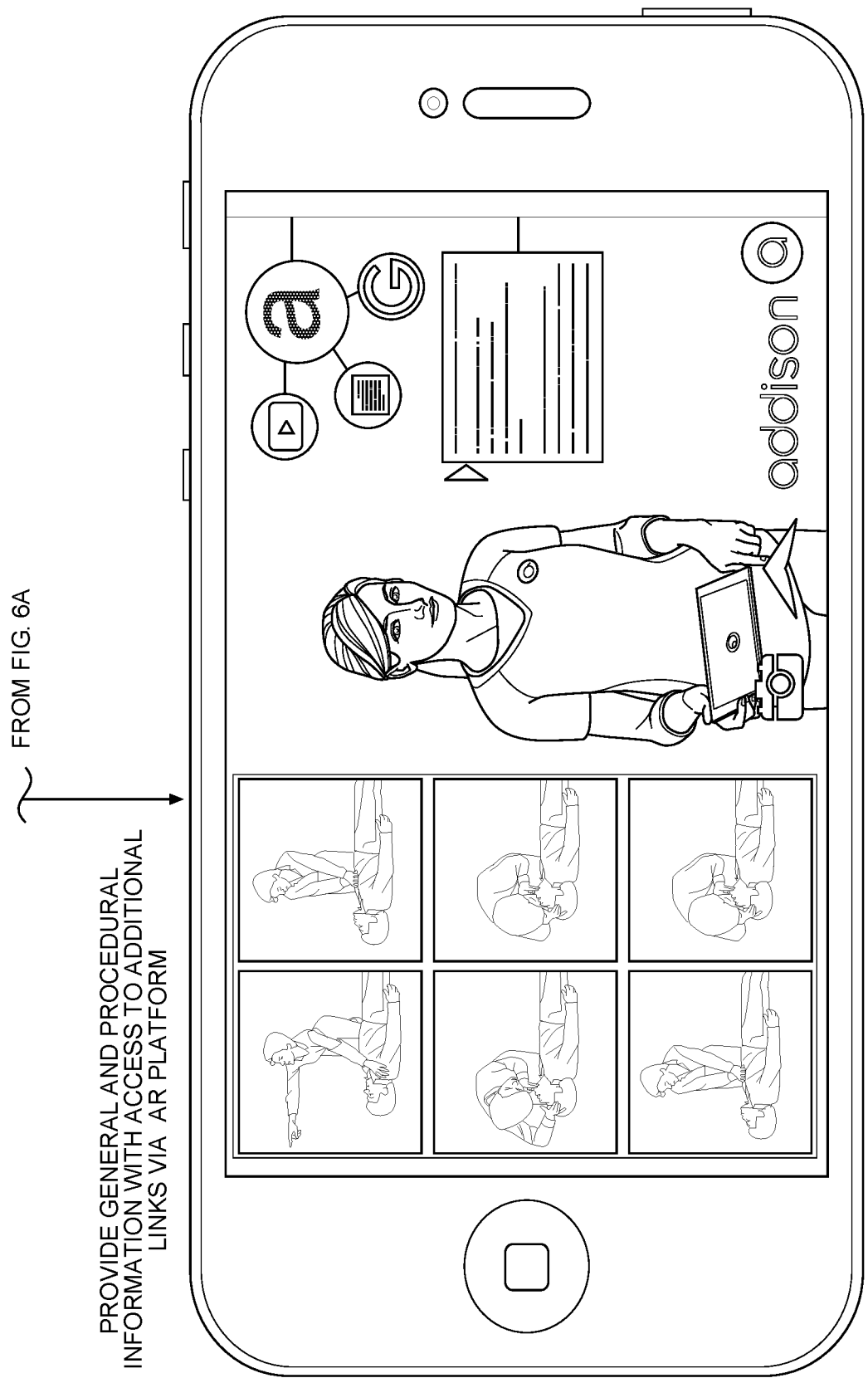

FIG. 6A and FIG. 6B illustrate exemplary graphical user interfaces for provision of emergency medical actions using a voice based, intelligent, augmented reality (AR) based on-demand medical assistant according to embodiments of the present technology. For example, FIG. 6A and FIG. 6B show access notification of emergency services based on interaction of the user 101 with embodiments of the present technology.

Figure 7:
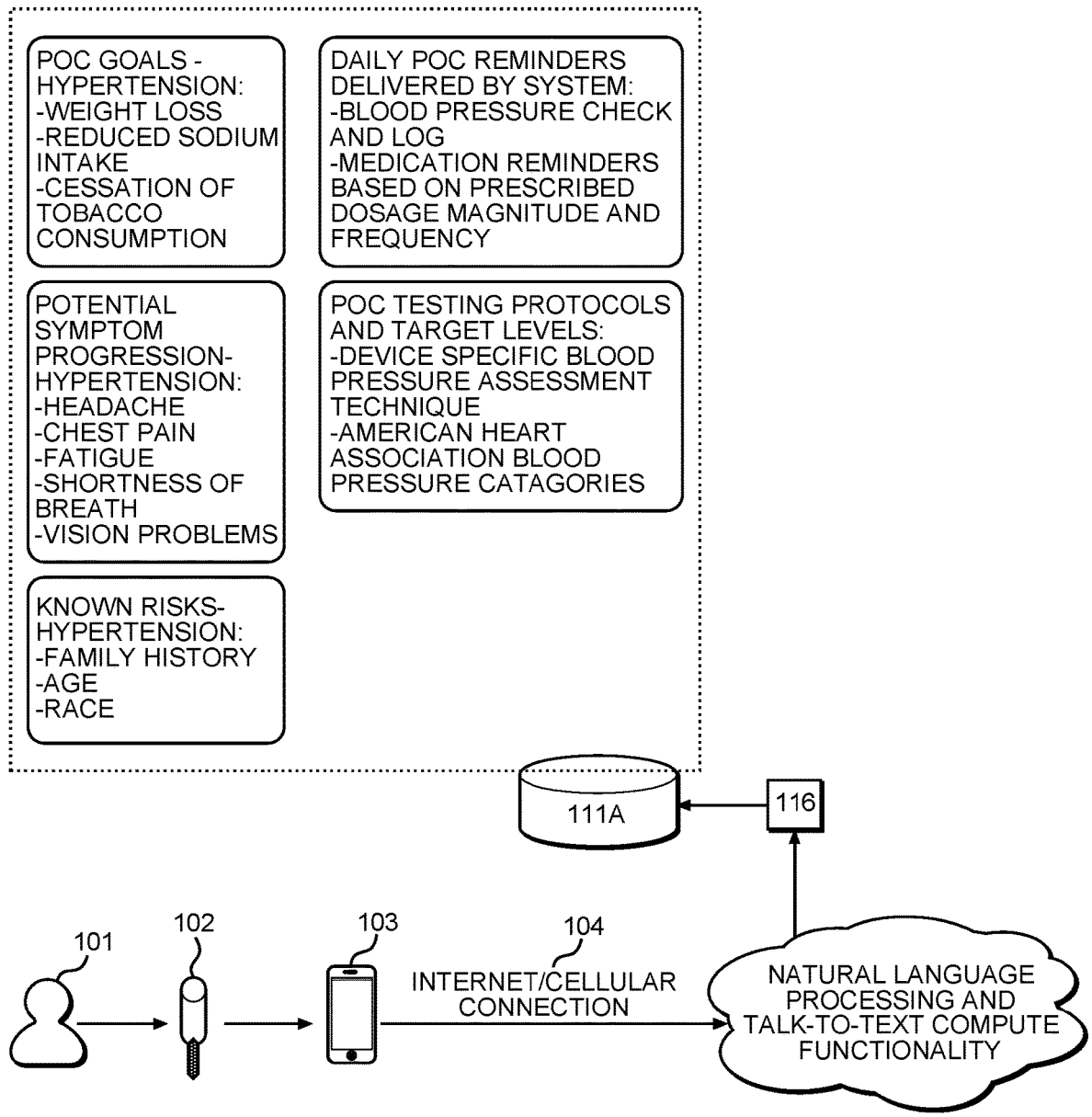
FIG. 7 shows a system for designating a plan of care using a voice based, intelligent, augmented reality (AR) based on-demand medical assistant according to embodiments of the present technology.

FIG. 7 shows a system for designating a plan of care using a voice based, intelligent, augmented reality (AR) based on-demand medical assistant according to embodiments of the present technology. FIG. 7 shows capacity of the present technology to provide the user 101 with a plan of care (POC) specific to their disease profile. For example, the present technology allows systems to assist individuals diagnosed with chronic medical problems to manage their disease process, yet still remain independent as much as possible. In order for these POCs to be successfully carried out, the user 101 provides basic information regarding their disease profile. As shown FIG. 7, the user 101 establishes their disease profile within the system through use of the conversational interface. After voice input processing and keyword identification by the keyword database 116, a data pathway to a medical database 111A is opened that sets in motion the development of a defined POC for the user 101. This POC is inclusive of: goals the user 101 should meet, basic reminders set to the specific POC, monitoring protocols associated with the specific disease profile, symptoms associated with disease progression, as well as medical testing needs, protocols, frequency, and targets.

In various embodiments of the present technology utilization of a web-browser based AR platform and conversational interface provides the user 101 with the opportunity to interact with the present technology in a manner that allows the system to take in data describing symptoms the user 101 is experiencing in real-time, compare those symptoms with known disease risks, and advise a course of action.

Embodiments of the present technology provide capacity for interacting with additional medical testing devices to take in, store, and assess various biomedical data. As such, the user 101 may be provided consistent feedback related to their disease status and to be guided through disease specific interventions that assist the user 101 in the management of their disease.

In various embodiments of the present technology, implementation of a POC specific to a user with diabetes is provided as an example. Following the POC establishment, the system interacts with the user 101 throughout the course of the day based on the defined characteristics of the POC. In this example, the user 101 has been diagnosed with diabetes and has set-up a POC based on their known risks and management goals. With the user 101 having the known risk factors of a lack of dietary adherence, inadequate blood glucose level monitoring, and a history of medication mismanagement, the system functions to deliver the POC: prompting the user 101 for nutritional planning for items that are appropriate for diabetics, consistently querying user 101 as to the last time of blood glucose testing, and medication management suggestion based on blood glucose test results.

In various embodiments of present technology systems provide the capacity to deliver health provider designated medical questionnaires and assessments to the user 101 without the need for a visit to the practitioner's office. Within the system, the user 101 has the ability to identify Health Insurance Portability and Accountability Act of 1996 (HIPPA) compliant third parties that can provide assessments for completion by the user 101. Once HIPPA compliant third parties are provided access by the user 101, the HIPPA compliant third parties have the capacity to request various medical assessments be delivered to the user 101. For this to occur, the HIPPA compliant third parties access a virtual assistant network via a network that indicates which follow-up/ancillary assessment(s) should be completed by the user 101. The system then notifies the user 101 of the prescribed assessment. Once notified the user 101 communicates with the system via the conversational interface and establishes a date and time to complete the prescribed assessment. Upon completion of the prescribed assessment by the user 101, the data are uploaded to cloud-based storage and can be accesses for evaluation by the prescribing practitioner. For example, the user 101 may be discharged from a hospital following total knee arthroplasty. Following discharge, HIPPA compliant third parties access a virtual assistant network via a connected device and request the user 101 to complete both the Oxford Knee Score questionnaire and/or the Physical Functional Ability Questionnaire. Additionally, a second HIPPA compliant third party requests the user 101 to provide general follow-up information related to how many times the user 101 walks per day, how far the user 101 can walk on average before needing to stop, and how often the user 101 consumes opioid based pain medication. These follow-up inputs are then transmitted to the user 101 via the system and after receipt of request, the user 101 completes the assessments in their home setting by way of the conversational interface and web-browser based AR platform. Once the requested follow-up assessments have been complete, the system transmits the data back to HIPPA compliant third parties and a virtual assistant network for assessment and evaluation.

Figure 8:
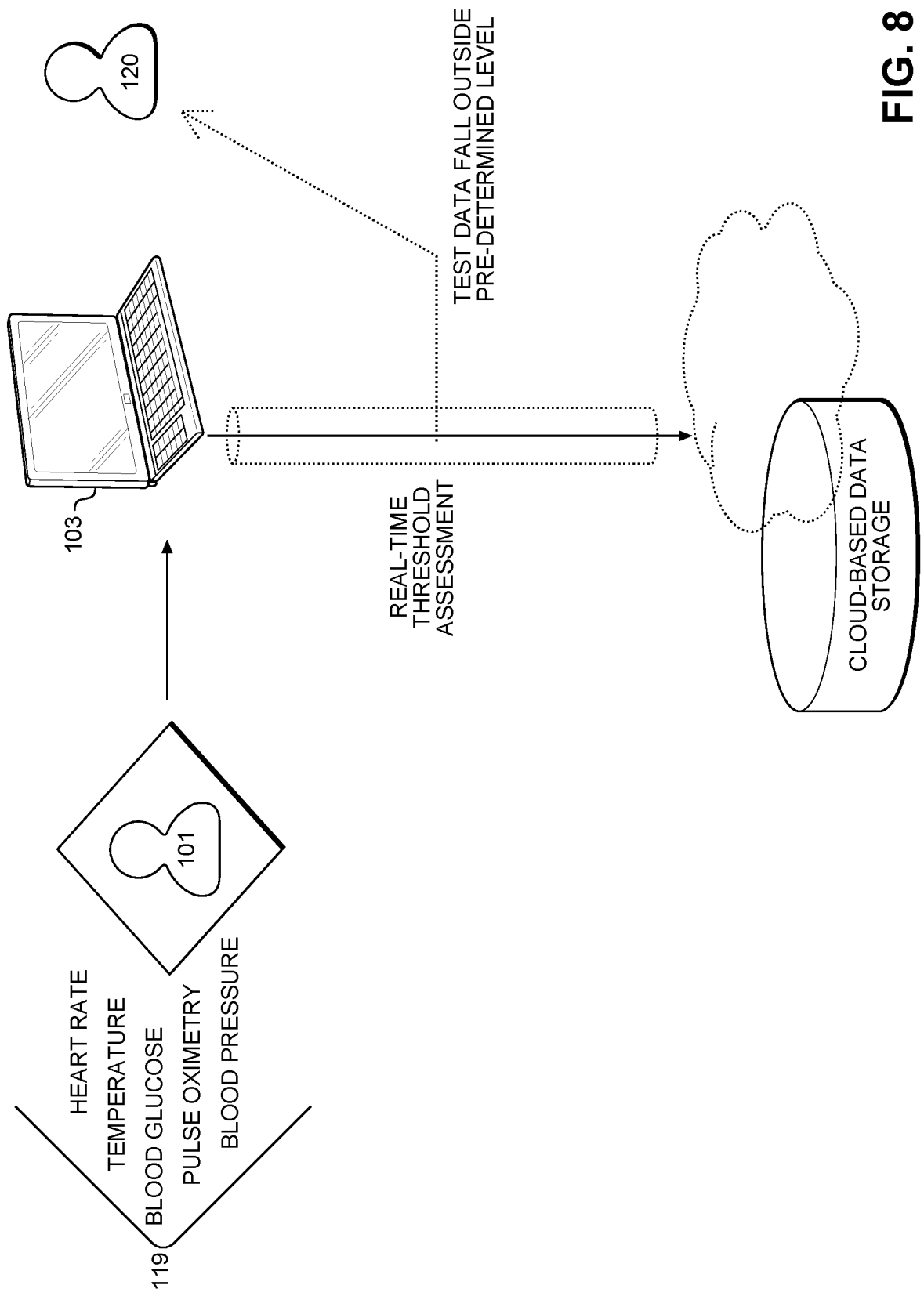
FIG. 8 shows a system for third-party contact protocol resulting from real-time data analysis using a voice based, intelligent, augmented reality (AR) based on-demand medical assistant displayed according to embodiments of the present technology.

FIG. 8 shows a system for third-party contact protocol resulting from real-time data analysis using a voice based, intelligent, augmented reality (AR) based on-demand medical assistant displayed according to embodiments of the present technology. FIG. 8 shows the ability to provide the user 101 with specific thresholds related to medical testing results that when exceeded, give rise to a notification of a provided third-party contact. As displayed in FIG. 8, a baseline threshold is set for specific characteristics of the disease profile associated with the user 101. Throughout the course of everyday life, the system prompts the user 101 to use the appropriate peripheral medical testing devices 119 to complete various medical tests prescribed as a result of their diagnosis. After testing is completed, these data are transmitted to and stored in a cloud-based database for longitudinal analysis specific to the user 101. During the transmission process, data is analyzed relative to a defined threshold in real-time. Regardless of threshold assessment results, the medical test data are transmitted to a cloud-based storage instance; however, when threshold analysis identifies medical test data that fall outside of the defined threshold, an immediate notification is transmitted to an indicated third-party contact 120. An example is shown in FIG. 9.

Figure 9:
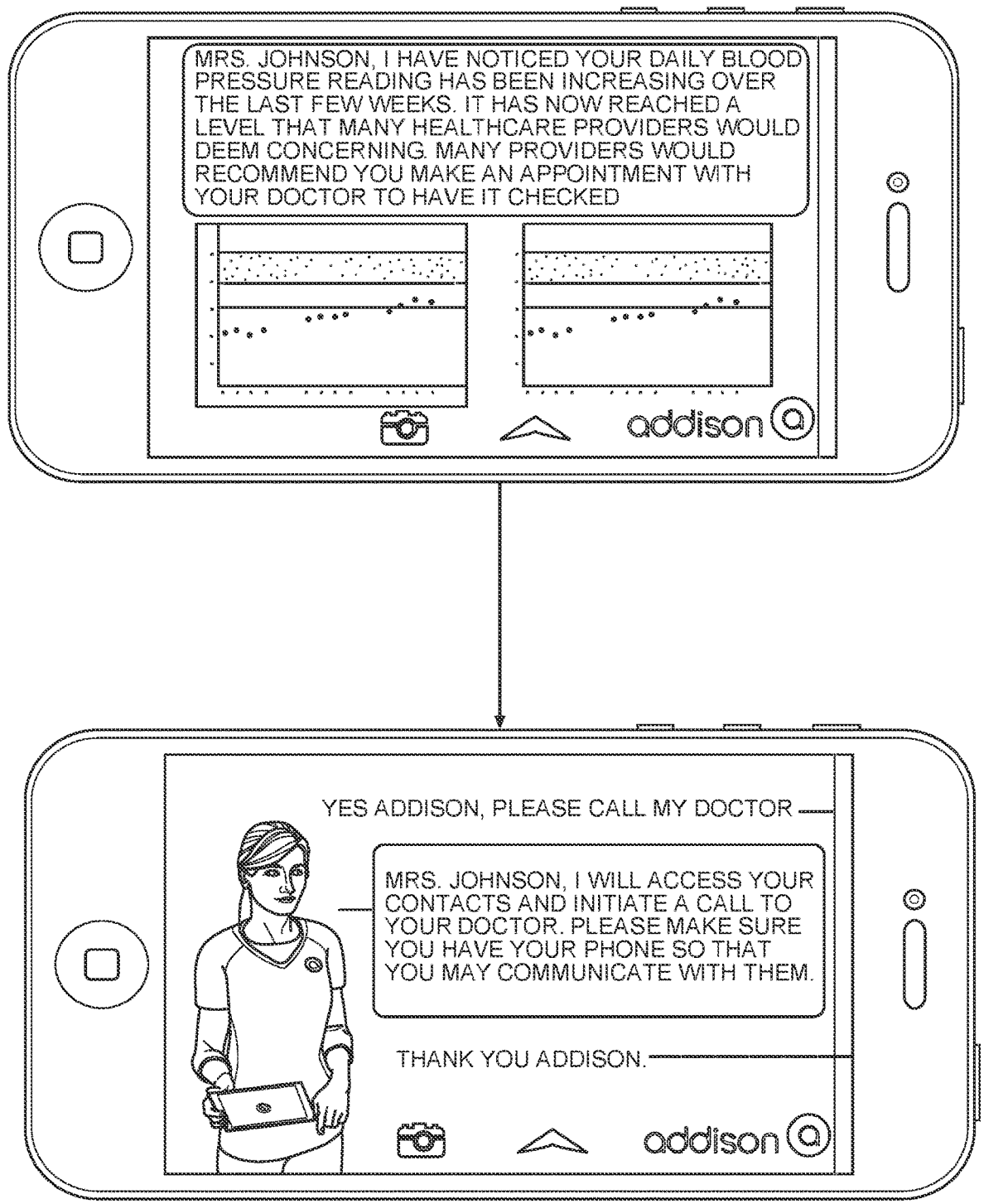
FIG. 9 illustrates exemplary graphical user interfaces for provision of emergency medical actions using a voice based, intelligent, augmented reality (AR) based on-demand medical assistant according to embodiments of the present technology.

FIG. 9 illustrates exemplary graphical user interfaces for provision of emergency medical actions using a voice based, intelligent, augmented reality (AR) based on-demand medical assistant according to embodiments of the present technology. FIG. 9 shows an assessment of pulse oximetry in cases of Chronic Obstructive Pulmonary Disease (COPD) and/or Congestive Heart Failure (CHF). Although in most cases, pulse oximetry levels between 95% and 100% are considered normal, in both COPD and CHF patients typically present with lower pulse oximetry levels that continue to decline as the disease progresses. By utilizing the system to consistently monitor, store and analyze pulse oximetry levels in real-time, progression of the disease can be remotely monitored. When pulse oximetry levels fall below the set threshold (e.g. 92%) the third-party notification protocol is activated allowing the defined contact (e.g., third-party contact 120) to be notified on a potential exacerbation.

Figure 10:
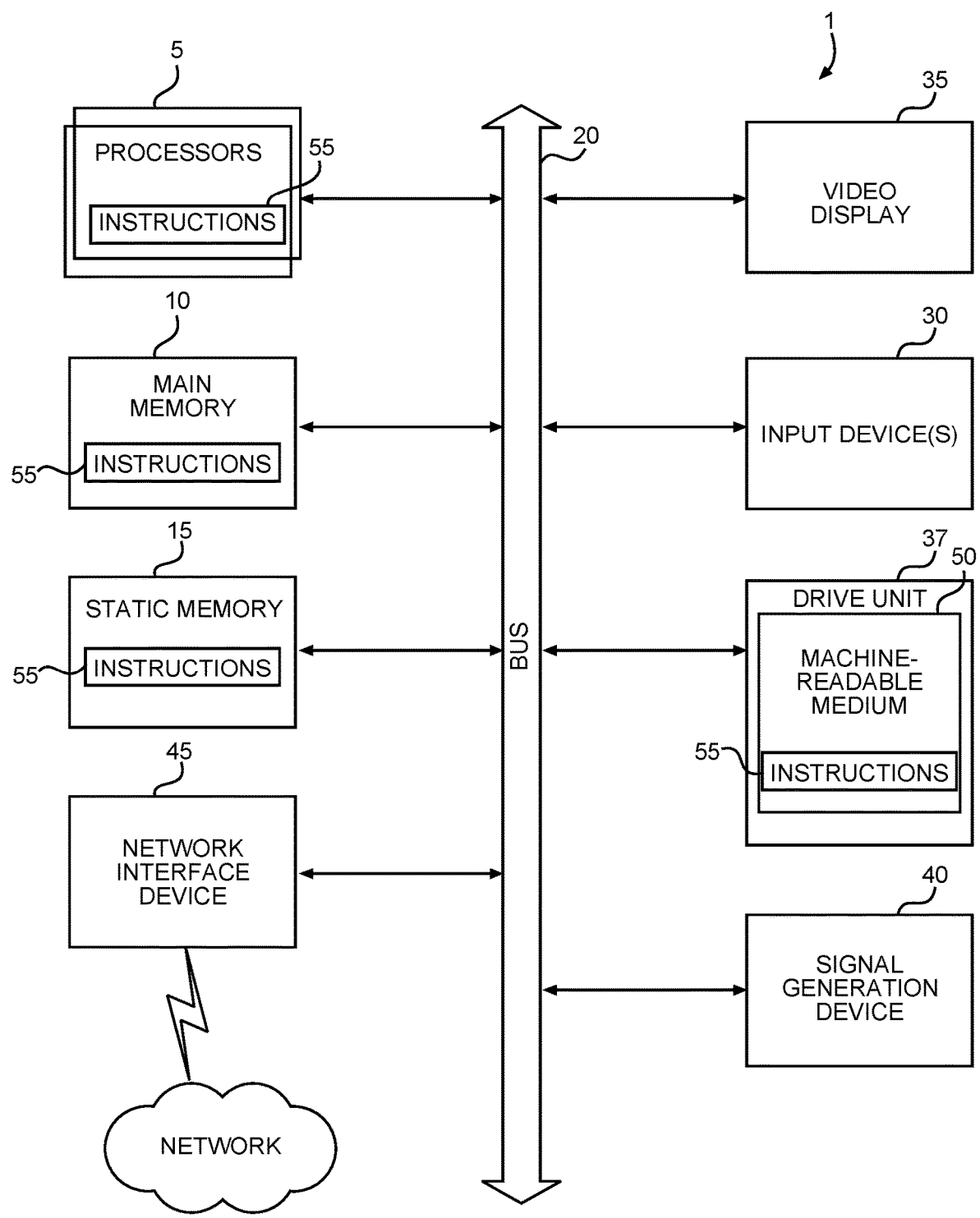
FIG. 10 illustrates an exemplary computer system that may be used for a voice based, intelligent, augmented reality (AR) based on-demand medical assistant according to embodiments of the present technology.

FIG. 10 illustrates an exemplary computer system that may be used for a voice based, intelligent, augmented reality (AR) based on-demand medical assistant according to embodiments of the present technology. FIG. 10 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

Thus, the technology for comprehensive fall risk assessment is disclosed. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for a voice based, intelligent, augmented reality (AR) based on-demand medical assistant, the method comprising:
   receiving health data of a user using medical testing equipment;
   storing the health data of the user in a retrieval database;
   receiving an audio input using a web-browser based AR, animated, conversational graphical user interface, the audio input comprising keywords;
   determining a domain of use based on processing the keywords of the audio input;
   processing the health data of the user, the keywords, and the domain of use to determine a medical assessment for the user;
   determining personalized medical services for the user based on the medical assessment;
   providing the user with access to the personalized medical services using the web-browser based AR, animated, conversational graphical user interface; and
   displaying a status of the personalized medical services to the user using the web-browser based AR, animated, conversational graphical user interface.

2. The method as recited in claim 1, further comprising:
   actively prompting the user for the health data using the web-browser based AR, animated, conversational graphical user interface.

3. The method as recited in claim 1, wherein the processing the health data of the user, the keywords, and the domain of use utilizes a medical and health vocabulary database.

4. The method as recited in claim 3, wherein the processing the health data of the user, the keywords, and the domain of use utilizes a secure cloud-based repository of user provided data, a public domain medical and health database, and a public domain informational repository.

5. The method as recited in claim 1, wherein the health data of the user comprises a baseline health level of the user.

6. The method as recited in claim 5, further comprising:
   determining when the baseline health level of the user deviates from a predetermined threshold.

7. The method as recited in claim 6, further comprising:
   displaying an alert to the user when the baseline health level of the user changes past a threshold via the web-browser based AR, animated, conversational graphical user interface.

8. The method as recited in claim 6, further comprising:
   sending an alert to a third-party medical service provider when the baseline health level of the user deviates from the predetermined threshold.

9. The method as recited in claim 1, wherein the health data of the user comprises a disease profile of the user.

10. The method as recited in claim 9, further comprising:
    providing the user with a treatment plan specific to the disease profile of the user using the web-browser based AR, animated, conversational graphical user interface.

11. A system for a voice based, intelligent, augmented reality (AR) based on-demand medical assistant, the system comprising:
    medical testing equipment for receiving health data of a user;
    a retrieval database for storing the health data of the user;
    a mobile device communicatively coupled to the medical testing equipment, the mobile device comprising:
    a web-browser based AR, animated, conversational graphical user interface for receiving audio input, the audio input comprising keywords;
    at least one processor; and a memory storing processor-executable instructions, wherein the at least one processor is configured to implement the following operations upon executing the processor-executable instructions:
determining a domain of use based on processing the keywords of the audio input;
processing the health data of the user, the keywords, and the domain of use to determine a medical assessment for the user;
determining personalized medical services for the user based on the medical assessment;
providing the user with access to the personalized medical services using the web-browser based AR, animated, conversational graphical user interface; and
displaying a status of the personalized medical services to the user using the web-browser based AR, animated, conversational graphical user interface.

12. The system as recited in claim 11, wherein the at least one processor is further configured to implement the operation of:
actively prompting the user for the health data using the web-browser based AR, animated, conversational graphical user interface.

13. The system as recited in claim 11, wherein the processing the health data of the user, the keywords, and the domain of use utilizes a medical and health vocabulary database.

14. The system as recited in claim 13, wherein the processing the health data of the user, the keywords, and the domain of use utilizes a secure cloud-based repository of user provided data, a public domain medical and health database, and a public domain informational repository.

15. The system as recited in claim 11, wherein the health data of the user comprises a baseline health level of the user.

16. The system as recited in claim 15, wherein the at least one processor is further configured to implement the operation of:
determining when the baseline health level of the user deviates from a predetermined threshold.

17. The system as recited in claim 16, wherein the at least one processor is further configured to implement the operation of:
displaying an alert to the user when the baseline health level of the user changes past a threshold via the web-browser based AR, animated, conversational graphical user interface.

18. The system as recited in claim 16, wherein the at least one processor is further configured to implement the operation of:
sending an alert to a third-party medical service provider when the baseline health level of the user deviates from the predetermined threshold.

19. A non-transitory computer readable medium having embodied thereon instructions being executable by at least one processor to perform a method for a voice based, intelligent, augmented reality (AR) based on-demand medical assistant, the method comprising:
receiving health data of a user using medical testing equipment;
storing the health data of the user in a retrieval database;
receiving an audio input using a web-browser based AR, animated, conversational graphical user interface, the audio input comprising keywords;
determining a domain of use based on processing the keywords of the audio input;
processing the health data of the user, the keywords, and the domain of use to determine a medical assessment for the user;
determining personalized medical services for the user based on the medical assessment;
providing the user with access to the personalized medical services using the web-browser based AR, animated, conversational graphical user interface; and
displaying a status of the personalized medical services to the user using the web-browser based AR, animated, conversational graphical user interface.

* * * * *